United States Patent
Allen et al.

(10) Patent No.: US 9,156,803 B2
(45) Date of Patent: Oct. 13, 2015

(54) SUCCINIC ANHYDRIDE FROM ETHYLENE OXIDE

(75) Inventors: Scott D. Allen, Ithaca, NY (US); Bernard Duane Dombek, Charleston, WV (US); Olan Stanley Fruchey, Hurricane, WV (US); Nye A. Clinton, Hurricane, WV (US)

(73) Assignee: NOVOMER, INC., Ithaca, NY (US)

( * ) Notice: Subject to any disclaimer, the term of this patent is extended or adjusted under 35 U.S.C. 154(b) by 0 days.

(21) Appl. No.: 13/819,969

(22) PCT Filed: Aug. 25, 2011

(86) PCT No.: PCT/US2011/049125
§ 371 (c)(1),
(2), (4) Date: Feb. 28, 2013

(87) PCT Pub. No.: WO2012/030619
PCT Pub. Date: Mar. 8, 2012

(65) Prior Publication Data
US 2013/0165670 A1    Jun. 27, 2013

Related U.S. Application Data

(60) Provisional application No. 61/377,917, filed on Aug. 28, 2010.

(51) Int. Cl.
*C07D 307/60*    (2006.01)
(52) U.S. Cl.
CPC .................... *C07D 307/60* (2013.01)
(58) Field of Classification Search
CPC ..................................... C07D 307/60
USPC ........................................ 549/233
See application file for complete search history.

(56) References Cited

U.S. PATENT DOCUMENTS

| 2,245,404 | A  | 6/1941 | Kise et al. |
| 5,096,470 | A  | 3/1992 | Krishnamurthy |
| 6,773,578 | B1 | 8/2004 | O'Rear et al. |
| 6,852,865 | B2 | 2/2005 | Coates et al. |
| 8,481,756 | B1 | 7/2013 | Coates et al. |

(Continued)

FOREIGN PATENT DOCUMENTS

| WO | WO-03050154 A2 | 6/2003 |
| WO | WO-2010/118128 A1 | 10/2010 |
| WO | WO 20121030619 A1 | 3/2012 |

OTHER PUBLICATIONS

International Preliminary Report on Patentability for PCT/US11/49125, dated Sep. 24, 2012, mailed from IPEA/US.

(Continued)

*Primary Examiner* — T. Victor Oh
(74) *Attorney, Agent, or Firm* — Choate, Hall & Stewart LLP; Charles E. Lyon; Kevin M. Henry

(57) ABSTRACT

Continuous flow systems and methods produce succinic anhydride by a double carbonylation of ethylene oxide with carbon monoxide and at least one catalyst. In some embodiments, the double carbonylation occurs using a single catalyst. In other embodiments, a first catalyst is used to promote the first carbonylation, and a second catalyst different from the first catalyst is used to promote the second carbonylation. The succinic anhydride is isolated from the product stream by crystallization and the catalyst is recycled to the reaction stream.

39 Claims, 1 Drawing Sheet

(56) References Cited

U.S. PATENT DOCUMENTS

2003/0162961 A1    8/2003    Coates et al.
2005/0014977 A1    1/2005    Drent et al.
2007/0213524 A1    9/2007    Coates et al.

OTHER PUBLICATIONS

International Search Report for PCT/US11/49125, dated Jan. 11, 2012, mailed from ISA/US.
Rowley et al., "Catalytic double carbonylation of epoxides to succinic anhydrides: catalyst discovery, reaction scope, and mechanism" *J. Am. Chem. Soc.* 129(16):4948-4960 (2007).
Written Opinion of the International Searching Authority for PCT/US11/49125, dated Jan. 11, 2012, mailed from ISA/US.
Extended European Search Report for EP11622380, 6 pages (Nov. 25, 2013).
International Search Report for PCT/US2013/025683, 2 pages (Apr. 23 2013).
Written Opinion for PCT/US2013/025683, 10 pages (Apr. 23, 2013).
Getzler, Y.D. et al., Catalytic Carbonylation of βLactones to Succinic Anhydrides, Journal of the American Chemical Society, 126(22):6842-6843 (2004).
Han-nou Kogaku, Baifukan Corp.. 10th print, 1-10, 49-61, 83-111 and 179-209 (1998).
Kagaku Kikai, 1st Edition: 4-5 and 336-340 (1967).
Kagaku-process Shusei (Chemical process aggregation), Tokyo Kagaku Dojin, 1st Edition: 1-6 (1970).
Zouho Kagakusouchi Hyakkajiten (Enlarged, Chemical Apparatus Encyclopedia, Kagaku-Kogyo Corp., 173 (1976).

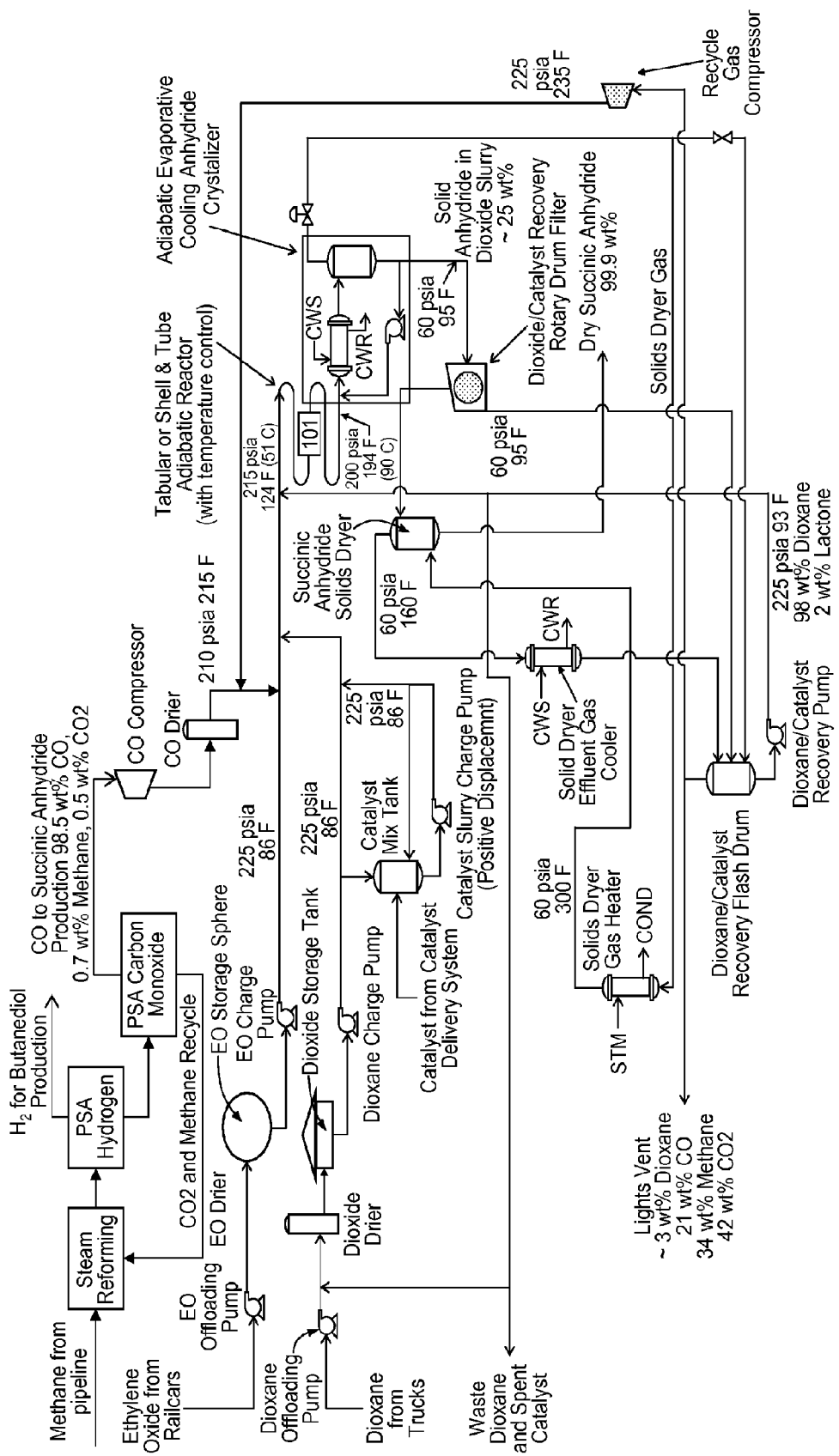

SUCCINIC ANHYDRIDE FROM ETHYLENE OXIDE

CROSS-REFERENCE TO RELATED APPLICATION

The present application is the National Stage application under 35 U.S.C. 371 of International Application No. PCT/US11/49125, filed Aug. 25, 2011, which claims priority to U.S. Provisional Patent Application Ser. No. 61/377,917, filed Aug. 28, 2010, the contents of each of which are herein incorporated by reference in their entireties.

BACKGROUND OF THE INVENTION

Acid anhydrides, in particular succinic anhydride, are valuable reactive intermediates commonly used in a variety of applications. For example, acid anhydrides are used in copolymers to produce biodegradable polyesters. Additionally, acid anhydrides are useful intermediates in organic synthesis because they are easily ring opened to form diacids or other derivatives. Succinic anhydride is particularly useful as a precursor to 4 carbon commodity chemicals such as tetrahydrofuran, gamma butyrolactone and 1,4-butanediol.

Previous production methods for acid anhydrides, including succinic anhydride, included dehydration of corresponding acids or hydrogenation of maleic anhydride. Additional production methods include catalyzed carbonylation of alkynes, alkenoic acids and lactones. Many of the methods suffered from low yield, production of many byproducts or lacked generality. Novel methods using more cost effective starting materials are sought.

U.S. Pat. No. 6,852,865 discloses a class of well-defined bimetallic catalysts of the general type [Lewis acid]$^+$[M(CO)$_x$]$^-$ for the ring-expanding carbonylation of strained heterocycles. Related catalysts can carbonylate the resulting β-lactones to succinic anhydrides in high yields while preserving stereochemical purity. Given the many syntheses of enantiomerically pure epoxides and the recent advances in epoxide carbonylation to β-lactones, subsequent carbonylation of these β-lactones constitutes a versatile two-step method for the stereoselective synthesis of succinic anhydrides. (Scheme 1).

Scheme 1

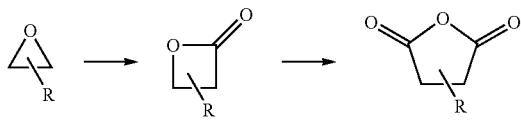

SUMMARY OF THE INVENTION

In various aspects, the present invention includes a method of synthesizing succinic anhydride including the steps of: feeding a reaction stream including ethylene oxide, at least one catalyst, at least one solvent, and carbon monoxide to a reaction vessel under reaction conditions to promote a double carbonylation of ethylene oxide to form succinic anhydride in the reaction stream in a continuous flow process; b) treating the reaction stream containing succinic anhydride to conditions that cause the succinic anhydride to crystallize such that the reaction stream includes crystallized succinic anhydride and a liquid phase including catalyst and solvent; c) separating the crystallized succinic anhydride from the liquid phase; and d) recycling the catalyst and the solvent to the reaction stream including the ethylene oxide.

In some embodiments, the solvent includes dioxane. In some embodiments, step b) occurs in an adiabatic evaporative cooling crystallizer. In some embodiments, step c) occurs in a rotary drum filter. In some embodiments, step d) includes the substep of feeding a solution including the catalyst and the solvent to a recovery flash drum to separate volatiles prior to returning the solution to the reaction stream. In some embodiments, the method further includes treating the solution by performing at least one step selected from the group consisting of: drying the solution; heating or cooling the solution; removing spent catalyst; adding solvent; and any combination of two or more of these.

In some embodiments, the first carbonylation reaction is performed at a pressure from about 50 psi to about 5000 psi. In some embodiments, the first carbonylation reaction is performed at a pressure from about 50 psi to about 2000 psi. In some embodiments, the first carbonylation reaction is performed at a pressure from about 200 psi to about 1000 psi. In some embodiments, the first carbonylation reaction is performed at a pressure from about 200 psi to about 600 psi.

In some embodiments, the first carbonylation reaction is performed at a temperature from about 0° C. to about 125° C. In some embodiments, the first carbonylation reaction is performed at a temperature from about 30° C. to about 100° C. In some embodiments, the first carbonylation reaction is performed at a temperature from about 40° C. to about 80° C.

In some embodiments, the at least one catalyst is a single catalyst. In some embodiments, the single catalyst is [(ClTPP)Al(THF)$_2$]$^+$[Co(CO)$_4$]$^-$, where ClTPP is meso-tetra (4-chlorophenyl)porphyrinato and THF is tetrahydrofuran. In some embodiments, the at least one catalyst includes a first catalyst selected to promote a first carbonylation of the double carbonylation and a second catalyst different from the first catalyst selected to promote a second carbonylation of the double carbonylation.

In some embodiments, the catalyst includes a metal carbonyl compound. In some embodiments, the metal carbonyl compound has the formula [QM$_y$(CO)$_w$]$^x$, where: Q is any ligand and need not be present; M is a metal atom; y is an integer from 1 to 6 inclusive; w is a number such as to provide the stable metal carbonyl; and x is an integer from −3 to +3 inclusive.

In some embodiments, M is selected from the group consisting of Ti, Cr, Mn, Fe, Ru, Co, Rh, Ni, Pd, Cu, Zn, Al, Ga, and In. In some embodiments, M is Co.

In some embodiments, the carbonylation catalyst further includes a Lewis acidic co-catalyst. In some embodiments, the metal carbonyl compound is anionic, and the Lewis acidic co-catalyst is cationic. In some embodiments, the metal carbonyl complex includes a carbonyl cobaltate and the Lewis acidic co-catalyst includes a metal-centered Lewis acid.

In some embodiments, the metal-centered Lewis acid is a metal complex of formula [M'(L)$_b$]$^{c+}$, where: M' is a metal; each L is a ligand; b is an integer from 1 to 6 inclusive; c is 1, 2, or 3; and where, if more than one L is present, each L may be the same or different. In some embodiments, M' is selected from the group consisting of: a transition metal, a group 13 or 14 metal, and a lanthanide. In some embodiments, M' is a transition metal or a group 13 metal. In some embodiments, M' is selected from the group consisting of aluminum, chromium, indium and gallium. In some embodiments, M' is aluminum. In some embodiments, M' is chromium.

In some embodiments, the Lewis acid includes a dianionic tetradentate ligand. In some embodiments, the dianionic tetradentate ligand is selected from the group consisting of: porphyrin derivatives; salen derivatives; dibenzotetramethyltetraaza[14]annulene (tmtaa) derivatives; phthalocyaninate derivatives; and derivatives of the Trost ligand. In some embodiments step c) includes the substep of filtering the reaction stream.

In various aspects, the present invention provides a succinic anhydride synthesis system including: a carbon monoxide source; an ethylene oxide source; a solvent source; a catalyst source; at least one reaction vessel fed with a reaction stream by the carbon monoxide source, the ethylene oxide source, the solvent source, and the catalyst source, the reaction stream including carbon monoxide, ethylene oxide, solvent, and catalyst; an adiabatic evaporative cooling crystallizer fed from the at least one reaction vessel; a rotary drum filter fed by the adiabatic evaporative cooling crystallizer; a solids dryer fed by the rotary drum filter; and a recovery flash drum fed by the adiabatic evaporative cooling crystallizer, the rotary drum filter, and the solids dryer, the recovery flash drum feeding recycled catalyst and solvent to the reaction stream.

In some embodiments, the reaction vessel includes a tubular reactor. In some embodiments, the reaction vessel includes a shell and tube adiabatic reactor. In some embodiments, the adiabatic evaporative cooling crystallizer includes a feed cooler and a crystallizer flash drum.

In some embodiments, the carbon monoxide source includes: a methane source; a steam reforming unit fed by the methane source; a hydrogen pressure swing adsorption unit fed by the steam reforming unit; a carbon monoxide pressure swing adsorption unit fed by the hydrogen pressure swing adsorption unit; a carbon monoxide compressor fed by the carbon monoxide pressure swing adsorption unit; and a carbon monoxide dryer fed by the carbon monoxide compressor.

In some embodiments, the solvent source includes: a solvent offloading pump; a solvent dryer fed by the solvent offloading pump; and a solvent storage tank fed by the solvent dryer; and a solvent charge pump fed by the solvent storage tank.

In some embodiments, the catalyst source includes a catalyst mix tank and a catalyst charge pump fed by the catalyst mix tank, wherein the solvent charge pump feeds solvent to the catalyst mix tank.

BRIEF DESCRIPTION OF THE DRAWING

FIG. 1 shows a process flow system for the production of succinic anhydride from ethylene oxide in one embodiment of the present invention.

DETAILED DESCRIPTION OF VARIOUS EMBODIMENTS OF THE INVENTION

Definitions

Definitions of specific functional groups and chemical terms are described in more detail below. For purposes of this invention, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

Certain compounds, as described herein may have one or more double bonds that can exist as either a Z or E isomer, unless otherwise indicated. The invention additionally encompasses the compounds as individual isomers substantially free of other isomers and alternatively, as mixtures of various isomers, e.g., racemic mixtures of enantiomers. In addition to the abovementioned compounds per se, this invention also encompasses compositions comprising one or more compounds.

As used herein, the term "isomers" includes any and all geometric isomers and stereoisomers. For example, "isomers" include cis- and trans-isomers, E- and Z-isomers, R- and S-enantiomers, diastereomers, (D)-isomers, (L)-isomers, racemic mixtures thereof, and other mixtures thereof, as falling within the scope of the invention. For instance, a compound may, in some embodiments, be provided substantially free of one or more corresponding stereoisomers, and may also be referred to as "stereochemically enriched."

The terms "halo" and "halogen" as used herein refer to an atom selected from fluorine (fluoro, —F), chlorine (chloro, —Cl), bromine (bromo, —Br), and iodine (iodo, —I). The term "halogenic" as used herein refers to a compound substituted with one or more halogen atoms.

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. Unless otherwise specified, aliphatic groups contain 1-30 carbon atoms. In certain embodiments, aliphatic groups contain 1-12 carbon atoms. In certain embodiments, aliphatic groups contain 1-8 carbon atoms. In certain embodiments, aliphatic groups contain 1-6 carbon atoms. In some embodiments, aliphatic groups contain 1-5 carbon atoms, in some embodiments, aliphatic groups contain 1-4 carbon atoms, in yet other embodiments aliphatic groups contain 1-3 carbon atoms, and in yet other embodiments aliphatic groups contain 1-2 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "heteroaliphatic," as used herein, refers to aliphatic groups wherein one or more carbon atoms are independently replaced by one or more atoms selected from the group consisting of oxygen, sulfur, nitrogen, phosphorus, or boron. In certain embodiments, one or two carbon atoms are independently replaced by one or more of oxygen, sulfur, nitrogen, or phosphorus. Heteroaliphatic groups may be substituted or unsubstituted, branched or unbranched, cyclic or acyclic, and include "heterocycle," "heterocyclyl," "heterocycloaliphatic," or "heterocyclic" groups.

The term "epoxide", as used herein, refers to a substituted or unsubstituted oxirane. Substituted oxiranes include monosubstituted oxiranes, disubstituted oxiranes, trisubstituted oxiranes, and tetrasubstituted oxiranes. Such epoxides may be further optionally substituted as defined herein. In certain embodiments, epoxides comprise a single oxirane moiety. In certain embodiments, epoxides comprise two or more oxirane moieties.

The term "acrylate" or "acrylates" as used herein refer to any acyl group having a vinyl group adjacent to the acyl carbonyl. The terms encompass mono-, di- and tri-substituted vinyl groups. Examples of acrylates include, but are not limited to: acrylate, methacrylate, ethacrylate, cinnamate (3-phenylacrylate), crotonate, tiglate, and senecioate. Because it is known that cylcopropane groups can in certain instances behave very much like double bonds, cyclopropane esters are specifically included within the definition of acrylate herein.

The term "polymer", as used herein, refers to a molecule of high relative molecular mass, the structure of which comprises the multiple repetition of units derived, actually or conceptually, from molecules of low relative molecular mass. In certain embodiments, a polymer is comprised of only one monomer species (e.g., polyethylene oxide). In certain embodiments, a polymer of the present invention is a copolymer, terpolymer, heteropolymer, block copolymer, or tapered heteropolymer of one or more epoxides.

The term "unsaturated", as used herein, means that a moiety has one or more double or triple bonds.

The term "alkyl," as used herein, refers to saturated, straight or branched-chain hydrocarbon radicals derived from an aliphatic moiety containing between one and six carbon atoms by removal of a single hydrogen atom. Unless otherwise specified, alkyl groups contain 1-12 carbon atoms. In certain embodiments, alkyl groups contain 1-8 carbon atoms. In certain embodiments, alkyl groups contain 1-6 carbon atoms. In some embodiments, alkyl groups contain 1-5 carbon atoms, in some embodiments, alkyl groups contain 1-4 carbon atoms, in yet other embodiments alkyl groups contain 1-3 carbon atoms, and in yet other embodiments alkyl groups contain 1-2 carbon atoms. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like.

The term "carbocycle" and "carbocyclic ring" as used herein, refers to monocyclic and polycyclic moieties wherein the rings contain only carbon atoms. Unless otherwise specified, carbocycles may be saturated, partially unsaturated or aromatic, and contain 3 to 20 carbon atoms. The terms "carbocycle" or "carbocyclic" also include aliphatic rings that are fused to one or more aromatic or nonaromatic rings, such as decahydronaphthyl or tetrahydronaphthyl, where the radical or point of attachment is on the aliphatic ring. In some embodiments, a carbocyclic groups is bicyclic. In some embodiments, a carbocyclic group is tricyclic. In some embodiments, a carbocyclic group is polycyclic. In certain embodiments, the terms "3- to 14-membered carbocycle" and "$C_{3-14}$ carbocycle" refer to a 3- to 8-membered saturated or partially unsaturated monocyclic carbocyclic ring, or a 7- to 14-membered saturated or partially unsaturated polycyclic carbocyclic ring.

Representative carbocyles include cyclopropane, cyclobutane, cyclopentane, cyclohexane, bicyclo[2,2,1]heptane, norbornene, phenyl, cyclohexene, naphthalene, spiro[4.5]decane, The term "aryl" used alone or as part of a larger moiety as in "aralkyl", "aralkoxy", or "aryloxyalkyl", refers to monocyclic and polycyclic ring systems having a total of five to 20 ring members, wherein at least one ring in the system is aromatic and wherein each ring in the system contains three to twelve ring members. The term "aryl" may be used interchangeably with the term "aryl ring". In certain embodiments of the present invention, "aryl" refers to an aromatic ring system which includes, but is not limited to, phenyl, biphenyl, naphthyl, anthracyl and the like, which may bear one or more substituents. Also included within the scope of the term "aryl", as it is used herein, is a group in which an aromatic ring is fused to one or more additional rings, such as benzofuranyl, indanyl, phthalimidyl, naphthimidyl, phenantriidinyl, or tetrahydronaphthyl, and the like. In certain embodiments, the terms "6- to 10-membered aryl" and "$C_{6-10}$ aryl" refer to a phenyl or an 8- to 10-membered polycyclic aryl ring.

The terms "heteroaryl" and "heteroar-", used alone or as part of a larger moiety, e.g., "heteroaralkyl", or "heteroaralkoxy", refer to groups having 5 to 14 ring atoms, preferably 5, 6, or 9 ring atoms; having 6, 10, or 14 electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, benzofuranyl and pteridinyl. The terms "heteroaryl" and "heteroar", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3b]-1,4-oxazin-3 (4H)-one. A heteroaryl group may be mono or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted. In certain embodiments, the term "5- to 14-membered heteroaryl" refers to a 5- to 6-membered heteroaryl ring having 1 to 3 heteroatoms independently selected from nitrogen, oxygen, or sulfur, or an 8- to 14-membered polycyclic heteroaryl ring having 1 to 4 heteroatoms independently selected from nitrogen, oxygen, or sulfur.

As used herein, the terms "heterocycle", "heterocyclyl", "heterocyclic radical", and "heterocyclic ring" are used interchangeably and refer to a stable 5- to 7-membered monocyclic or 7-14-membered bicyclic heterocyclic moiety that is either saturated, partially unsaturated, or aromatic and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl). In some embodiments, the term "3- to 14-membered heterocycle" refers to a 3- to 8-membered saturated or partially unsaturated monocyclic heterocyclic ring having 1 to 2 heteroatoms independently selected from nitrogen, oxygen, or sulfur, or a 7- to 14-membered saturated or partially unsaturated polycyclic heterocyclic ring having 1-3 heteroatoms independently selected from nitrogen, oxygen, or sulfur.

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; $-(CH_2)_{0-4}R^\circ$; $-(CH_2)_{0-4}OR^\circ$; $-O-(CH_2)_{0-4}C(O)OR^\circ$; $-(CH_2)_{0-4}CH(OR^\circ)_2$; $-(CH_2)_{0-4}SR^\circ$; $-(CH_2)_{0-4}Ph$, which may be substituted with $R^\circ$; $-(CH_2)_{0-4}O(CH_2)_{0-1}Ph$ which may be substituted with $R^\circ$; $-CH=CHPh$, which may be substituted with $R^\circ$; $-NO_2$; $-CN$; $-N_3$; $-(CH_2)_{0-4}N(R^\circ)_2$; $-(CH_2)_{0-4}N(R^\circ)C(O)R^\circ$; $-N(R^\circ)C(S)R^\circ$; $-(CH_2)_{0-4}N(R^\circ)C(O)NR^\circ_2$; $-N(R^\circ)C(S)NR^\circ_2$; $-(CH_2)_{0-4}N(R^\circ)C(O)OR^\circ$; $-N(R^\circ)N(R^\circ)C(O)R^\circ$; $-N(R^\circ)N(R^\circ)C(O)NR^\circ_2$; $-N(R^\circ)N(R^\circ)C(O)OR^\circ$; $-(CH_2)_{0-4}C(O)R^\circ$; $-C(S)R^\circ$; $-(CH_2)_{0-4}C(O)OR^\circ$; $-(CH_2)_{0-4}C(O)N(R^\circ)_2$; $-(CH_2)_{0-4}C(O)SR^\circ$; $-(CH_2)_{0-4}C(O)OSiR^\circ_3$; $-(CH_2)_{0-4}OC(O)R^\circ$; $-OC(O)(CH_2)_{0-4}SR-$, $SC(S)SR^\circ$; $-(CH_2)_{0-4}SC(O)R^\circ$; $-(CH_2)_{0-4}C(O)NR^\circ_2$; $-C(S)NR^\circ_2$; $-C(S)SR^\circ$; $-SC(S)SR^\circ$; $-(CH_2)_{0-4}OC(O)NR^\circ_2$; $-C(O)N(OR^\circ)R^\circ$; $C(O)C(O)R^\circ$; $-C(O)CH_2C(O)R^\circ$; $-C(NOR^\circ)R^\circ$; $-(CH_2)_{0-4}SSR^\circ$; $-(CH_2)_{0-4}S(O)_2R^\circ$; $-(CH_2)_{0-4}S(O)_2OR^\circ$; $-(CH_2)_{0-4}OS(O)_2R^\circ$; $-S(O)_2NR^\circ_2$; $-(CH_2)_{0-4}S(O)R^\circ$; $-N(R^\circ)S(O)_2NR^\circ_2$; $-N(R^\circ)S(O)_2R^\circ$; $-N(OR^\circ)R^\circ$; $-C(NH)NR^\circ_2$; $-P(O)_2R^\circ$; $-P(O)R^\circ_2$; $-OP(O)R^\circ_2$; $-OP(O)(OR^\circ)_2$; $SiR^\circ_3$; $-(C_{1-4}$ straight or branched)alkylene)O$-N(R^\circ)_2$; or $-(C_{1-4}$ straight or branched)alkylene)C(O)ON(R^\circ_2$, wherein each $R^\circ$ may be substituted as defined below and is independently hydrogen, $C_{1-8}$ aliphatic, $CH_2Ph$, $-O(CH_2)_{0-1}Ph$, or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or polycyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, $-(CH_2)_{0-2}R^\bullet$, -(haloR$^\bullet$), $-(CH_2)_{0-2}OH$, $-(CH_2)_{0-2}OR^\bullet$, $-(CH_2)_{0-2}CH(OR^\bullet)_2$; $-O(haloR^\bullet)$, $-CN$, $-N_3$, $-(CH_2)_{0-2}C(O)R^\bullet$, $-(CH_2)_{0-2}C(O)OH$, $-(CH_2)_{0-2}C(O)OR^\bullet$, $-(CH_2)_{0-4}C(O)N(R^\circ)_2$; $-(CH_2)_{0-2}SR^\bullet$, $-(CH_2)_{0-2}SH$, $-(CH_2)_{0-2}NH_2$, $-(CH_2)_{0-2}NHR^\bullet$, $-(CH_2)_{0-2}NR^\bullet_2$, $-NO_2$, $-SiR^\bullet_3$, $-OSiR^\bullet_3$, $-C(O)SR^\bullet$, $-(C_{1-4}$ straight or branched alkylene)C(O)OR$^\bullet$, or $SSR^\bullet$ wherein each $R^\bullet$ is unsubstituted or where preceded by "halo" is substituted only with one or more halogens, and is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, $-O(C(R*_2))_{2-3}O-$, or $-S(C(R*_2))_{2-3}S-$, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: $-O(CR*_2)_{2-3}O-$, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, $-R^\bullet$, -(haloR$^\bullet$), $-OH$, $-OR^\bullet$, $-O(haloR^\bullet)$, $-CN$, $-C(O)OH$, $C(O)OR^\bullet$, $-NH_2$, $-NHR^\bullet$, $-NR^\bullet_2$, or $-NO_2$, wherein each $R^\bullet$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include $-R^\dagger$, $-NR^\dagger_2$, $-C(O)R^\dagger$, $-C(O)OR^\dagger$, $-C(O)C(O)R^\dagger$, $-C(O)CH_2C(O)R^\dagger$, $-S(O)_2R^\dagger$, $-S(O)_2NR^\dagger_2$, $-C(S)NR^\dagger_2$, $-C(NH)NR^\dagger_2$, or $-N(R^\dagger)S(O)_2R^\dagger$; wherein each $R^\dagger$ is independently hydrogen, $C_{1-6}$ aliphatic which may be substituted as defined below, unsubstituted $-OPh$, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^\dagger$ are independently halogen, $-R^\bullet$, -(haloR$^\bullet$), $-OH$, $-OR^\bullet$, $-O(haloR^\bullet)$, $-CN$, $-C(O)OH$, $-C(O)OR^\bullet$, $-NH_2$, $-NHR^\bullet$, $-NR^\bullet_2$, or $-NO_2$, wherein each $R^\bullet$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

As used herein, the term "catalyst" refers to a substance the presence of which increases the rate of a chemical reaction, while not being consumed or undergoing a permanent chemical change itself.

Double Carbonylation

Methods of the present invention achieve the double carbonylation of epoxides, whereby each epoxide molecule reacts with two molecules of carbon monoxide to produce an acid anhydride (e.g., a cyclic anhydride). The double carbonylation is facilitated by the catalysts and conditions of the present invention. The double carbonylation is preferably achieved in a single process using reaction conditions under which both carbonylation reactions occur without the necessity of isolating or purifying the product of the first carbonylation.

Scheme 2

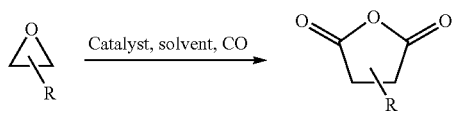

With known catalysts and conditions, a useful process according to Scheme 2 has previously been unachievable, since the two steps (lactone formation from an epoxide and anhydride formation from a lactone) were found to have different and often mutually-exclusive reaction requirements. One embodiment of the present invention encompasses catalyst/solvent combinations that enable this process to succeed in a single pot reaction format. The present invention provides catalysts and methods that enable the double carbonylation of epoxides to provide acid anhydride products. In some embodiments, the process is a continuous process. In some embodiments, the acid anhydride product is crystallizable in order to separate it from the catalyst or catalysts. In one embodiment, the epoxide is ethylene oxide and the product is succinic anhydride, although the epoxide may be any epoxide that forms an acid anhydride derivative that is crystallizable. For example, the epoxide may be propylene oxide, where the product is methylsuccinic anhydride.

The catalysts described herein may be used to successfully transform epoxides into acid anhydrides in a continuous flow process. In some embodiments, the transformation occurs in a single reaction (i.e. in a single reaction vessel under one set of reaction conditions). The reaction vessel is can be a continuous flow reaction vessel. In other embodiments, the transformation occurs under continuous flow using more than one reaction vessel but without isolation of the intermediate lactone product. In some embodiments, the double carbonylation occurs using a single catalyst.

In some embodiments, the double carbonylation uses a single catalyst for both carbonylation steps. In some embodiments, two catalysts are used in which one catalyst is selected for improved performance in the first carbonylation step and the other is selected for improved performance in the second carbonylation step. In other embodiments, a first catalyst is used to promote the first carbonylation, and a second catalyst different from the first catalyst is used to promote the second carbonylation. In these embodiments, the catalysts and solvents are preferably chosen to optimize the reaction rate of the particular carbonylation step.

In some embodiments of the present invention, the transformation occurs in a single continuous flow reaction vessel with controlled reaction conditions in the reaction vessel or along the length of the reaction vessel. In some embodiments, the reaction conditions as the reaction stream enters the reaction vessel are different from the reaction conditions as the product stream leaves the reaction vessel such that the reaction conditions as the reaction stream enters the reaction vessel promote the first carbonylation, and the reaction conditions as the product stream leaves the reaction vessel promote the second carbonylation. Several aspects of the reaction conditions have been found to affect the outcome of these processes including, but not limited to, the presence of a reaction solvent, the concentration of the substrate, the amount of catalyst present, and the pressure and temperature at which the reaction is performed.

FIG. 1 shows a process flow system for the production of succinic anhydride from ethylene oxide in a preferred embodiment of the present invention. In this embodiment, the epoxide is transferred from an epoxide source, (e.g., railcars), by an offloading pump to a storage tank, where it is stored until needed. The epoxide is preferably ethylene oxide (EO) in this embodiment. The solvent, (e.g., dioxane), is transferred from a solvent source (e.g., trucks), by an offloading pump to a dryer before being stored in a storage tank. The catalyst is stored in a mix tank. Carbon monoxide (CO) from a carbon monoxide source is compressed in a compressor and dried in a dryer. In certain embodiments, the carbon monoxide, along with hydrogen, is produced by steam reforming methane from a methane source (e.g., a pipeline). The hydrogen is separated, for example by pressure swing adsorption (PSA) and may be used for other purposes, for example butanediol production. The CO is purified by a further PSA prior to compression, with carbon dioxide and methane being recycled for further steam reforming. The solvent is supplied by a charge pump, which sends a portion of the solvent to the catalyst mix tank to form a slurry or solution. Where a slurry is produced, it may be supplied by a charge pump to combine with additional solvent to form a catalyst-solvent solution. The EO is supplied by a charge pump, and the CO is applied to the EO prior to mixing with the catalyst-solvent solution to form the reaction stream. The reaction stream is fed to a tubular or shell and tube adiabatic reactor with temperature control.

The product stream exiting the reactor can then be sent to a separation process to isolate the acid anhydride product from the solvent, catalyst, by-products and un-reacted reactants. The separation can be one step or a combination of steps. Further, the separation can be a solid-liquid, liquid-liquid or liquid-gas separation. In one embodiment, the product stream exiting the reactor is fed to an adiabatic evaporative cooling anhydride crystallizer including a crystallizer feed cooler followed by a crystallizer flash drum. This produces a volatiles stream and a slurry of solid succinic anhydride along with the catalyst in solvent. The catalyst is preferably highly soluble in the solvent such that it remains dissolved in the slurry. In one embodiment, the slurry is fed to a solvent/catalyst recovery rotary drum filter, where the liquid solution is separated from the solid succinic anhydride. The solid succinic anhydride stream is sent to a succinic anhydride solids dryer, which is preferably a rotary kiln, from which it exits as the product. The volatiles stream from the crystallizer flash drum is cooled and the remaining gaseous phase is sent to a solids dryer gas heater, where it is dried and heated prior to being sent to the succinic anhydride solids dryer for drying the succinic anhydride. The gas stream exiting the succinic anhydride solids dryer is sent to a gas cooler prior to being fed to a solvent/catalyst recovery flash drum along with the liquid component of the cooled volatiles stream and the liquid solution exiting the dioxane/catalyst recovery rotary drum filter. The solvent/catalyst liquid exiting the recovery flash drum is sent by a recovery pump to the reaction stream before entering the reactor. The gas stream exiting the recovery flash drum is vented in part and compressed in part in a compressor and recycled back into the CO feed stream.

Epoxides & Reactants

The methods are generally applicable and a wide range of epoxide starting materials can be used. The epoxide substrates (and by extension the lactone intermediates and anhydride products) may be unsubstituted (i.e., ethylene oxide) or may be monosubstituted, vicinally disubstituted (either cis or trans). The methods can also be applied to geminally disubstituted, trisubstituted or tetrasubstituted epoxides though these substrates react more slowly and tend to give lower yields of anhydride. The substituent(s) on the epoxide can be any that is compatible with the reaction conditions described herein.

In certain embodiments, the epoxide has the formula I:

The R group and any other chemical variable appearing in the Schemes and structures described herein encompass those chemical moieties and functional groups that would be recognized by one having skill in the art of organic chemistry as being compatible with the structure and function of the molecules bearing those chemical variables. Exemplary functional groups include substituted and unsubstituted cyclic and acyclic hydrocarbon moieties, substituted and unsubstituted cyclic and acyclic heteroatom-containing moieties, as well as common functional groups comprising heteroatoms, halogens, and metalloid elements. To further define the range of suitable groups certain definitions are provided below. Nonetheless, it is to be understood that these definitions are meant to be representative and the absence of a specific group or moiety in the definitions below is not necessarily meant to exclude such groups or to imply that such a group is not encompassed by the present invention.

In any case where a chemical variable is shown attached to a bond that crosses a bond of ring (for example as shown for R above, $R^d$ in certain ligands below, etc.), this means that one or more such variables are optionally attached to the ring having the crossed bond. Each R group on such a ring can be attached at any suitable position, this is generally understood to mean that the group is attached in place of a hydrogen atom on the parent ring. This includes the possibility that two R groups can be attached to the same ring atom. Furthermore, when more than one R group is present on a ring, each may be the same or different than other R groups attached thereto, and each group is defined independently of other groups that may be attached elsewhere on the same molecule, even though they may be represented by the same identifier.

In one embodiment of the epoxides of formula I, each R group can be independently selected from the group consisting of: (a) $C_1$ to $C_{20}$ alkyl; (b) $C_2$ to $C_{20}$ alkenyl; (c) $C_2$ to $C_{20}$ alkynyl; (d) up to a $C_{12}$ carbocycle; (e) up to a $C_{12}$ heterocycle; (f) —$C(R^{13})_zH_{(3-z)}$; and (g) a polymer chain. Two or more R groups may be taken together with the carbon atoms to which they are attached to form one or more rings, and any of (a) through (e) may optionally be further substituted with one or more F groups.

F at each occurrence can be independently selected from the group consisting of: halogen; —$OR^{10}$; —$OC(O)R^{13}$; —$OC(O)OR^{13}$; —$OC(O)NR^{11}R^{12}$; —CN; —CNO; —$C(O)R^{13}$; —$C(O)OR^{13}$; —$C(O)NR^{11}R^{12}$; —$C(R^{13})_zH_{(3-z)}$; —$NR^{11}C(O)R^{10}$; —$NR^{11}C(O)OR^{10}$; —NCO; —$NR^{12}SO_2R^{13}$; —$S(O)_xR^{13}$; —$S(O)_2NR^{11}R^{12}$; —$NO_2$; —$N_3$; —$(CH_2)_kR^{14}$; —$(CH_2)_k$—Z—$R^{16}$; and —$(CH_2)_k$—Z—$(CH_2)_m$—$R^{14}$.

$R^{10}$ at each occurrence can be independently selected from the group consisting of: —$C(R^{13})_zH_{(3-z)}$; $C_1$ to $C_{12}$ alkyl; $C_2$ to $C_{12}$ alkenyl; $C_2$ to $C_{12}$ alkynyl; up to a $C_{1-2}$ carbocycle; up to a $C_{1-2}$ heterocycle; —$S(O)_2R^{13}$; —$Si(R^{15})_3$; —H; and a hydroxyl protecting group.

$R^{11}$ and $R^{12}$ at each occurrence can be independently selected from the group consisting of: —H; $C_1$ to $C_{12}$ alkyl; $C_2$ to $C_{12}$ alkenyl; $C_2$ to $C_{12}$ alkynyl; and $C(R^{13})_zH_{(3-z)}$. $R^{11}$ and $R^{12}$; when both present, can optionally be taken together with the atom to which they are attached to form a 3- to 10-membered ring.

$R^{13}$ at each occurrence can be independently selected from the group consisting of: —H; $C_1$ to $C_{12}$ alkyl; $C_2$ to $C_{12}$ alkenyl; $C_2$ to $C_{12}$ alkynyl; up to a $C_{12}$ carbocycle; and up to a $C_{12}$ heterocycle.

$R^{14}$ at each occurrence can be independently selected from the group consisting of: halogen; —$OR^{10}$; —$OC(O)R^{13}$; —$OC(O)OR^{13}$; —$OC(O)NR^{11}R^{12}$; —CN; —CNO; —$C(R^{13})_zH_{(3-z)}$; —$C(O)R^{13}$; —$C(O)OR^{13}$; —$C(O)NR^{11}R^{12}$; —$NR^{11}C(O)R^{13}$; —$NR^{11}C(O)OR^{10}$; —$NR^{11}SO_2R^{13}$; —NCO; —$N_3$; —$NO_2$; —$S(O)_xR^{13}$; —$SO_2NR^{11}R^{12}$; up to a $C_{12}$ heterocycle; and up to a $C_{12}$ carbocycle.

$R^{15}$ at each occurrence can be independently selected from the group consisting of: $C_1$ to $C_6$ alkyl; $C_2$ to $C_6$ alkenyl; $C_2$ to $C_6$ alkynyl; and up to $C_{12}$ substituted or unsubstituted carbocycle.

$R^{16}$ at each occurrence can be independently selected from the group consisting of: $C_1$ to $C_{12}$ alkyl; $C_2$ to $C_{12}$ alkenyl; $C_2$ to $C_{12}$ alkynyl; up to a $C_{12}$ heterocycle; up to a $C_{12}$ carbocycle; and —$C(R^{13})_zH_{(3-z)}$.

Z is a divalent linker and can be selected from the group consisting of: —$(CH=CH)_a$—; —$(CH=CH)_a$—; —C(O)—; —$C(=NOR^{11})$—; —$C(=NNR^{11}R^{12})$—; —O—; —$N(R^{11})$—; —$N(C(O)R^{13})$—; —$S(O)_x$—; a polyether; and a polyamine.

a can be 1, 2, 3, or 4.

k can be an integer from 1 to 8 inclusive.

m can be an integer from 1 to 8 inclusive.

x can be 0, 1, or 2.

z can be 1, 2, or 3.

It is to be understood that the present invention encompasses the use of epoxides which comprise any combination of these variable definitions. For example, as discussed in below, we have applied the methods to the following representative unsubstituted and monosubstituted epoxides: ethylene oxide (4), propylene oxide (6), 1,2-epoxybutane (8); 1,2-epoxyhexane (10); 1,2-epoxydodecane (12); cyclohexyl oxirane (14); n-butyl glycidyl ether (16); tert-butyldimethylsilyl glycidyl ether (18); benzyl glycidyl ether (20); 10,11-epoxyundecan-1-ol (22); 4,5-epoxypentyl butyrate (24); 5,6-epoxyhexanenitrile (26); N,N-dimethyl-10,11-undecylamide (28); 1,2-epoxy-5-hexene (30); 1,2-epoxy-7-octene (32); (2,3-epoxypropyl)benzene (34); styrene oxide (36); and 1,2, 7,8-diepoxyoctane (38). Ethylene oxide (4) and propylene oxide (6) are of particular commercial interest.

As discussed below, we have also applied the methods to the following representative disubstituted epoxides: cis-2,3-epoxybutane (40); trans-2,3-epoxybutane (42); trans-3,4-epoxyhexane (44); and trans-2,3-epoxyoctane (46).

As discussed below, we have also applied the methods to the following representative enantiomerically enriched epoxides: (R)-propylene oxide ((R)-6); (S)-1,2-epoxyhexane ((S)-10); and (R)-benzyl glycidyl ether ((R)-20).

These representative epoxides demonstrate that the methods are applicable to a range of substituted epoxide substrates including those containing ethers, alcohols, esters, amides, nitriles, silyl ethers, alkenes and aromatics. It is to be understood that these lists are not exhaustive, other functional groups can also be present, for example ketone and acetal substituted epoxides have been successfully employed.

Additional reactants can include carbon monoxide, or a mixture of carbon monoxide and another gas. In some embodiments, carbon monoxide is provided in a mixture with hydrogen (e.g., Syngas). The ratio of carbon monoxide and hydrogen can be any ratio, including by not limited to 1:1, 1:2, 1:4, 1:10, 10:1, 4:1, or 2:1. In some embodiments, the carbon monoxide is provided in a mixture containing other gases. The carbon monoxide sources include but are not limited to: wood gas, producer gas, coal gas, town gas, manufactured gas, hygas, Dowson gas or water gas, among others. In some embodiments, the carbon monoxide is provided by steam reforming from another hydrocarbon (e.g., methane) as described above. The carbon monoxide can be purified by pressure swing absorption to reduce the quantity of other gases in the steam reforming effluent. In some embodiments, the carbon monoxide is provided at super-atmospheric pressure. The quantity of carbon monoxide should be supplied to effect efficient conversion of the epoxide starting material to an acid anhydride.

Catalysts

The present invention encompasses the use of carbonylation catalysts comprising a Lewis acid in combination with a transition metal carbonyl complex. The term Lewis acid as used herein refers to any electrophilic species that is capable of accepting an electron pair and that is not a Brønsted-Lowry acid.

In certain embodiments, the catalyst comprises a complex of formula [Lewis acid]$^{4+}$ {[QT(CO)$_v$]$^{s-}$}$^t$ where Q is any ligand and need not be present; T is a transition metal; u is an integer from 1 to 6 inclusive; s is an integer from 1 to 4 inclusive; t is a number such that t multiplied by s equals u; and v is an integer from 1 to 9 inclusive. For example, in one embodiment u and s are both 1. In another embodiment u and s are both 2. In certain embodiments, v is an integer from 1 to 4 inclusive. In one embodiment, v is 4.

Lewis Acids

In certain embodiments, the Lewis acid portion of the catalyst includes an element from groups 3 through 14 of the periodic table or contains a lanthanide metal. Useful Lewis acids may either be neutral (e.g., compounds such as $AlCl_3$, $CrCl_2$, $CrCl_3$, $ZnCl_2$, $BF_3$, $BCl_3$, $Yb(OTf)_3$, $FeCl_2$, $FeCl_3$, $CoCl_2$, etc.) or cationic (for instance, metal complexes of the formula [M(L)$_b$]$^{c+}$ where M is a metal, each L is a ligand, b is an integer from 1 to 6 inclusive, and c is 1, 2, or 3, and where, if more than one L is present, each L may be the same or different). A broad array of metallo Lewis acids have been found applicable to the present invention. In certain embodiments, M is a transition metal, a group 13 or 14 metal, or a lanthanide. Transition metals and group 13 metals are of particular interest. For example, in certain embodiments, M is aluminum, chromium, indium or gallium. In some embodiments, M is aluminum or chromium.

Similarly, a range of ligands (L) can be present in the metallo Lewis acid component of the catalyst. In certain embodiments the ligand can be a dianionic tetradentate ligand.

Suitable ligands include, but are not limited to: porphyrin derivatives 1, salen derivatives 2, dibenzotetramethyltetraaza [14]annulene (tmtaa) derivatives 3, phthalocyaninate derivatives 4, and derivatives of the Trost ligand 5. In certain embodiments, porphyrin, salen and tmtaa derivatives are of particular utility. In some cases, a mixture of more than one Lewis acid component can be present in the catalyst. Exemplary definitions for the R groups appearing in structures 1 through 5 are more fully described below.

In certain embodiments, the metal complex includes a metal M and a ligand L of formula 1:

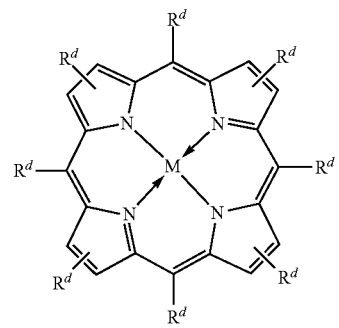

where $R^d$ at each occurrence is independently selected from the group consisting of: —H; $C_1$-$C_{12}$ alkyl; $C_2$-$C_{12}$ alkenyl; $C_2$-$C_{12}$ alkynyl; halogen; $OR^{10}$; —OC(O)$R^{13}$; —OC(O)O$R^{13}$; —OC(O)NR$^{11}$R$^{12}$; —CN; —CNO; —C(O)R$^{13}$; —C(R$^{13}$)$_z$H$_{(3-z)}$; —C(O)OR$^{13}$; —C(O)NR$^{11}$R$^{12}$; —NR$^{11}$R$^{12}$; —NR$^{11}$C(O)R$^{10}$; —NR$^{11}$C(O)OR$^{13}$; —NR$^{11}$SO$_2$R$^{13}$; —NCO; —N$_3$; —NO$_2$; —S(O)$_x$R$^{13}$; —SO$_2$NR$^{11}$R$^{12}$; —C(R$^{13}$)$_z$H$_{(3-z)}$; —(CH$_2$)$_k$R$^{14}$; —(CH$_2$)$_k$—Z—R$^{16}$—; and —(CH$_2$)$_k$—Z—(CH$_2$)$_m$—R$^{14}$, and where $R^{10}$, $R^{11}$, $R^{12}$, $R^{13}$, $R^{14}$, $R^{16}$, Z, k, m, x, and z are as defined above.

In certain embodiments, the metal complex includes a metal M and a ligand L of formula 2:

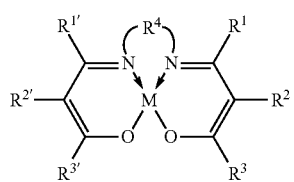

where $R^1$ and $R^{1'}$ are independently selected from the group consisting of: —H; $C_1$ to $C_{12}$ alkyl; $C_2$ to $C_{12}$ alkenyl; $C_2$ to $C_{12}$ alkynyl; —C(R$^{13}$)$_z$H$_{(3-z)}$; —(CH$_2$)$_k$R$^{14}$; and —(CH$_2$)$_k$—Z—R$^{14}$, where $R^2$, $R^{2'}$, $R^3$, and $R^{3'}$ are independently selected from the group consisting of: (i) $C_1$-$C_{12}$ alkyl; (ii) $C_2$-$C_{12}$ alkenyl; (iii) $C_2$-$C_{12}$ alkynyl; (iv) up to a $C_{12}$ carbocycle; (v) up to a $C_{12}$ heterocycle; (vi) —(CH$_2$)$_k$R$^{14}$; (vii) $R^{20}$; and (viii) —C(R$^{13}$)$_z$H$_{(3-z)}$, where each of (i) through (v) may optionally be further substituted with one or more $R^{20}$ groups; and where $R^2$ and $R^3$, and $R^{2'}$ and $R^{3'}$ may optionally be taken together with the carbon atoms to which they are attached to form one or more rings which may in turn be substituted with one or more $R^{20}$ groups; and where $R^4$ is selected from the group consisting of:

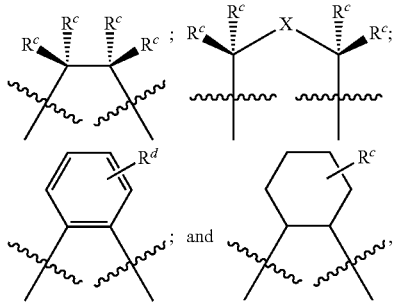

where X is a divalent linker selected from the group consisting of: —N($R^{11}$)—; —O—; —S(O)$_x$—; —(CH$_2$)$_k$—; —C(O)—; —C(=NOR$^{10}$)—; —C(R$^c$)$_2$—; a polyether; a $C_3$ to $C_8$ substituted or unsubstituted carbocycle; and a $C_1$ to $C_8$ substituted or unsubstituted heterocycle, where $R^d$ is as defined above, where $R^c$ at each occurrence is independently selected from the group consisting of: (a) $C_1$-$C_{12}$ alkyl; (b) $C_2$-$C_{12}$ alkenyl, (c) $C_2$-$C_{12}$ alkynyl; (e) up to a $C_{12}$ carbocycle, (f) up to a $C_{12}$ heterocycle; (g) $R^{20}$; (h) —C($R^{13}$)$_z$H$_{(3-z)}$; and (i) —H, where two or more $R^c$ groups may be taken together with the carbon atoms to which they are attached to form one or more rings, where when two $R^c$ groups are attached to the same carbon atom, they may be taken together to form a moiety selected from the group consisting of: a 3- to 8-membered spirocyclic ring; a carbonyl (C=O), an oxime) (C=NOR$^{10}$); a hydrazone (C=NNR$^{11}$R$^{12}$); and imine (C=NR$^{11}$); and an alkenyl group (C=CR$^{11}$R$^{12}$), and where any of (a) through (f) may optionally be further substituted with one or more $R^{20}$ groups, where $R^{20}$ at each occurrence is independently selected from the group consisting of: —H; halogen; —OR$^{10}$; —OC(O)R$^{13}$; —OC(O)OR$^{13}$; —OC(O)NR$^{11}$R$^{12}$; —CN; —CNO; —C(O)R$^{13}$; —C(O)OR$^{13}$; —C(O)NR$^{11}$R$^{12}$; —C(R$^{13}$)$_z$H$_{(3-z)}$; —NR$^{11}$R$^{12}$; —NR$^{11}$C(O)R$^{10}$; —NR$^{11}$C(O)OR$^{10}$; —NCO; —NR$^{12}$S(O)$_2$R$^{13}$; —S(O)$_2$NR$^{11}$R$^{12}$; —NO$_2$; —N$_3$; —(CH$_2$)$_k$R$^{14}$; —(CH$_2$)$_k$—Z—R$^{16}$; and —(CH$_2$)$_k$—Z—(CH$_2$)$_m$—R$^{14}$, and where $R^{10}$, $R^{11}$, $R^{12}$, $R^{13}$, $R^{14}$, $R^{16}$, Z, k, m, x, and z are as defined above.

In certain embodiments, the metal complex includes a metal M and a ligand L of formula 3:

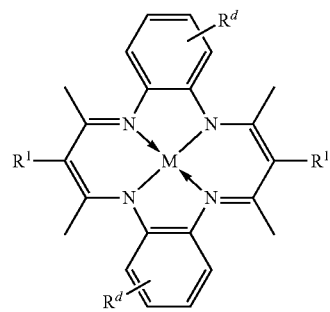

where $R^d$ is as defined above, where $R^1$ at each occurrence is independently selected from the group consisting of: —H; $C_1$ to $C_{12}$ alkyl; $C_2$ to $C_{12}$ alkenyl; $C_2$ to $C_{12}$ alkynyl; —C(R$^{13}$)$_z$H$_{(3-z)}$; —(CH$_2$)$_k$R$^{14}$; and —(CH$_2$)$_k$—Z—R$^{14}$, and where $R^{13}$, $R^{14}$, Z, k, and z are as defined above.

In certain embodiments, the metal complex includes a metal M and a ligand L of formula 4:

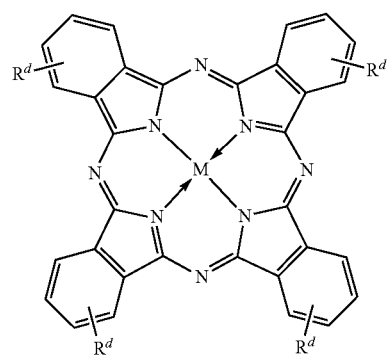

where $R^d$ is as defined above.

In certain embodiments, the metal complex includes a metal M and a ligand L of formula 5:

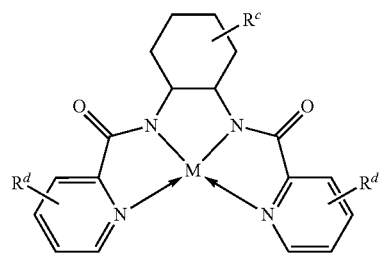

where $R^c$ and $R^d$ are as defined above.

Transition Metal Carbonyl Complexes

The transition metal carbonyl complex included in the catalyst may be neutral or anionic. In certain embodiments, the metal carbonyl complex is anionic, e.g., monoanionic carbonyl complexes of metals from groups 5, 7 or 9 of the periodic table or dianionic carbonyl complexes of metals from groups 4 or 8 of the periodic table. In certain embodiments, the metal carbonyl complex contains a metal from groups 7 or 9 of the periodic table, e.g., cobalt, manganese or rhodium. Examples of suitable anionic metal carbonyl complexes include, but are not limited to: $[Co(CO)_4]^-$ and $[Mn(CO)_5]^-$. In certain embodiments $[Co(CO)_4]^-$ may be used. In some cases, a mixture of two or more transition metal carbonyl complexes can be present in the catalyst.

While the metal carbonyl complexes disclosed herein are generally binary metal carbonyl complexes (i.e., they have the formula $M(CO)_y$ and consist only of a metal and carbonyl ligands) this is not a limiting requirement of the present invention, and the use of mixed ligand metal carbonyl complexes is also contemplated. For example, a bidentate phosphine ligand may be present along with the carbonyl ligands. It is also anticipated that under some reaction conditions, mixed ligand carbonyl complexes may be formed in situ from the binary complexes during the reaction. Whether added or formed in situ, catalysts containing mixed ligand carbonyl complexes are encompassed by the present invention.

The stoichiometry of the Lewis acid and the metal carbonyl complex components of the catalyst encompassed by the present invention can be varied. Typically, the two components are present in a ratio that balances the charges of the two species. For example, if the Lewis acid is a monocation and the metal carbonyl complex is a dianion, then they can be present in a charge-balancing ratio of 2:1 (i.e., 2 [Lewis acid]$^+$+[M(CO)$_x$]$^{2-}$). In some cases, if the charge of the carbonyl complex exceeds that of the Lewis acid component—either because there is a stoichiometric excess of the former, or because the Lewis acid is a neutral species—then the excess negative charge of the carbonyl complex can be balanced by the presence of a group 1 or 2 metal cation, or by a non-metallic cation such as an ammonium, phosphonium, or arsonium cation.

In some cases, the metal atom of the metallo Lewis acid can be coordinated to one or more additional neutral coordinating ligands (for instance to satisfy the metal atom's coordination valence) one such ligand that is particularly preferred is tetrahydrofuran (THF), it will be understood however that many other solvents and other ligands such as are well known in the art may also fulfill this role without departing from the present invention. It will also be realized that under reaction conditions, the coordinating ligands can be replaced by reagents, products, intermediates or solvents that may be present. Such in situ-generated species are also encompassed by the present invention. As with many catalytic processes, the structure of the specific catalyst added to the reaction will not always be the active species.

In a related vein, catalysts suitable for the processes of the present invention can be formed in situ from individual components. For example, the Lewis acid and the metal carbonyl complex can be added separately to the reaction vessel in which the reaction is performed. In one specific example of this, instead of adding aluminum tetrakis-(4-chlorophenyl)-porphine bis-tetrahydrofuran tetracarbonylcobaltate (1c) as the catalyst, one can separately add aluminum tetrakis-(4-chlorophenyl)-porphine chloride and sodium tetracarbonyl cobaltate. In a similar procedure, an aluminum porphyrin tetrafluoroborate compound (TPP(Al)$^+$BF$_4^-$) was combined in situ with bis(triphenylphosphine)iminium tetracarbonyl cobaltate (PPN$^+$Co(CO)$_4^-$) to provide the active catalyst. It is thus to be understood that such combinations of reagents that will produce a Lewis acid/metal carbonyl pair in situ are within the scope of the present invention.

Without wishing to be bound by any theory or to thereby limit the scope of the invention, it is believed that catalysts combining a Lewis acid component that is cationic and a metal carbonyl complex that is anionic are particularly suitable for carbonylation processes of the present invention. It is further believed that Lewis acid/metal carbonyl combinations that have a propensity to form non-ionic associations may be less effective (for instance if a covalent or coordinate covalent bond is prone to form between the metals of the two components). In such cases it can be advantageous to add additional components that prevent this association. As one example, when the Lewis acid component is based on an indium porphyrin complex, and the metal carbonyl component is tetracarbonyl cobaltate, the carbonylation reaction is improved by addition of triphenylphosphine. Again without being bound by theory or thereby limiting the scope of the present invention, the phosphine is believed to coordinate with the indium and thereby disrupt its propensity to bind to the cobaltate component of the catalyst.

In some cases, it has been found advantageous to have an excess of the transition metal carbonyl component of the catalyst present in the reaction mixture. For instance, the metal carbonyl complex can be present in an excess ranging from about 2-fold to about 10-fold. If there is an excess of an anionic metal carbonyl complex relative to the Lewis acid, then the negative charge can be balanced as described above, the excess negative charge is balanced by the presence of an alkali or alkaline earth metal.

Solvents

With respect to solvents (i.e., reaction solvents), methods of the invention have been found to be improved by the presence of a solvent. In some embodiments, solvents are of a low to moderate polarity. In some embodiments, the solvent fully dissolves the epoxide substrate to provide a reaction mixture in which the catalyst employed is at least partially soluble. Additionally, in some aspect, the solvents lack reactive functional groups.

In some embodiments, the solvent includes a Lewis base. The term Lewis base as used herein refers to any nucleophilic species that is capable of donating an electron pair. In some embodiments, the presence of suitable solvents can suppress the formation of polymeric side products and, in some cases, increase the rate and/or yield of the reaction.

In certain embodiments, the Lewis base is distinct from the epoxide. In other embodiments, the Lewis base is the epoxide (i.e., the reaction is performed in neat epoxide). Indeed, while the use of non-epoxide solvents may lead to higher yields, we have found that certain catalysts allow double carbonylation to be achieved in neat epoxide.

In certain embodiments, the solvent used will fully dissolve the epoxide and provide a reaction mixture in which the catalyst employed is at least partially soluble. Suitable solvents may include ethers, ketones, aromatic hydrocarbons, halocarbons, esters, nitriles, and some alcohols. For example, without limitation, a suitable solvent may include: 1,4-dioxane; 1,3-dioxane; tetrahydrofuran; tetrahydropyran; dimethoxyethane; glyme; diethyl ether; t-butyl methyl ether; 2,5-dimethyl tetrahydrofuran; ethyl acetate; propyl acetate; butyl acetate; acetone; 2-butanone; cyclohexanone; toluene; acetonitrile; and difluorobenzene. In some embodiments, the solvent includes 1,4-dioxane, toluene, and/or dimethoxyethane. In one embodiment, solvent includes 1,4-dioxane. Mixtures of two or more of the above solvents are also useful, and in some cases may be preferred to a single solvent. For example, mixtures of toluene and 1,4-dioxane are useful.

In certain embodiments, we have found that Lewis bases of low to moderate polarity improve the performance of the reaction over polar solvents. Thus, in certain embodiments, the solvent may include a Lewis base which is less polar than 1,3-dioxane ($\in$=dielectric constant at 20 C=13.6). In certain embodiments, the solvent includes a Lewis base which is less polar than ortho-difluorobenzene ($\in$=13). In certain embodiments, the solvent includes a Lewis base which is less polar than meta-difluorobenzene ($\in$=5). In certain embodiments, the solvent includes a Lewis base with substantially the same polarity as 1,4-dioxane ($\in$=2.2).

In certain embodiments, we have found that Lewis bases of low to moderate electron donicity improve the performance of the reaction over strongly donating Lewis bases. Thus, in certain embodiments, the solvent may include a Lewis base with lower electron donicity than tetrahydrofuran. In certain embodiments, the solvent may include a Lewis base with lower electron donicity than 2-methyltetrahydrofuran. In certain embodiments, the solvent may include a Lewis base with lower electron donicity than 2,5-dimethyltetrahydrofuran. In certain embodiments, the solvent may include a Lewis base with higher electron donicity than difluorobenzene. In certain embodiments, the solvent may include a Lewis base with higher electron donicity than toluene. In certain embodiments, the solvent may include a Lewis base with substantially the same electron donicity as 1,4-dioxane.

It will be appreciated that while 1,4-dioxane appears to produce particularly high yields of anhydride when used in combination with various catalysts that are described in the Examples, other solvents and mixtures of solvents (including solvents and mixtures that are not explicitly disclosed) may be used with these catalysts. While some of these combinations may produce lower yields they remain within the scope of the present invention. It will also be appreciated that present invention is in no way limited to the representative catalysts that are exemplified in this application. In particular, now that we have demonstrated that high yield double carbonylation is possible through appropriate selection of catalyst and solvent, those skilled in the art will recognize that our teachings can be generalized to other catalyst/solvent combinations.

In general, highly polar, reactive or protic solvents are generally inferior or unsuitable for processes of the present invention. Inferior solvents include ionic liquids, chlorinated hydrocarbons, sulfolane, dimethylsulfoxide, formamide, pyridine, and the like.

The solvent is preferably added in an amount sufficient to achieve an epoxide concentration of from about 0.1M to about 20M, for example from about 0.1M to about 5M or about from 0.5M to about 2M.

Reaction Conditions

The conditions for the carbonylation reaction are selected based on a number of factors to effect conversion of the epoxide to an acid anhydride. Temperature, pressure, and reaction time influence reaction speed and efficiency. Additionally, the ratio of reactants to each other and to the catalyst effect reaction speed and efficiency.

In some embodiments, the reaction temperature can range from between about −20° C., to about 600° C. In some embodiments, the reaction temperature is about −20° C., about 0° C., about 20° C., about 40° C., about 60° C., about 80° C., about 100° C., about 200° C., about 300° C., about 400° C., about 500° C. or about 600° C. In some embodiments, the reactants, catalyst and solvent are supplied to the reactor at standard temperature, and then heated in the reactor. In some embodiments, the reactants are pre-heated before entering the reactor. In some embodiments, the reactants are cooled before entering the reactor.

Turning next to the effect of temperature, in certain embodiments the reaction temperature was found to affect the rate and outcome of processes of the invention. At higher temperatures the reaction proceeds more quickly than at lower temperatures, but the propensity to form reaction by-products may increase.

In some embodiments, the reaction pressure can range from between about 50 psig to about 5000 psig. In some embodiments, the reaction pressure is about 100 psig, about 200 psig, about 300 psig, about 400 psig, about 500 psig, about 600 psig, about 700 psig, about 800 psig, about 900 psig, or about 1000 psig. In some embodiments, the pressure ranges from about 50 psig to about 2000 psig. In some embodiments, the pressure ranges from about 100 psig to 1000 psig. In some embodiments, the pressure ranges from about 200 psig to about 800 psig. In some embodiments, the reaction pressure is supplied entirely by the carbon monoxide. For example, the reactants, catalyst and solvent are charged to the reactor at atmospheric pressure, or under a vacuum, and carbon monoxide is added to the reactor to increase pressure to the reaction pressure. In some embodiments, all reactants, solvent and catalyst are supplied to the reactor at reaction pressure.

Optionally, the atmosphere under which the reaction is conducted can include other gasses. Such other gasses can include, for example, hydrogen, methane, nitrogen, carbon dioxide, air, and trace amounts of steam. The present invention also specifically encompasses processes in which other carbon monoxide-containing gas streams provide the atmosphere under which the reaction is conducted, as described above. Undesirable side-product can be minimized at higher reaction temperatures by performing the reaction at relatively high carbon monoxide pressures. In some cases therefore, the optimal temperature will be dependent upon the pressure at which the reaction is conducted. At high carbon monoxide pressures, e.g., greater than about 400 psi, elevated temperatures were found to be advantageous for the reaction (e.g., up to about 120° C.). In some cases, the reaction may be conducted at a temperature ranging from about 40° C. to about 80° C. To avoid by-product formation, the reaction mixture may be pressurized with CO while at a low temperature (e.g., <0° C.) and heating is introduced only after CO has been allowed to contact the reaction mixture. If minimization of by-product is desired, the CO pressure may be applied for a period of time prior to heating the mixture (e.g., at least 5 minutes prior to heating).

In some embodiments, the ratio of catalyst to epoxide is selected, based on other reaction conditions, so that the reaction proceeds in an economical and time-feasible manner. In some embodiments, the ratio of catalyst to epoxide is about 1:10000 on a molar basis. In some embodiments, the molar ratio of catalyst to epoxide is about 1:5000, is about 1:2500, is about 1:2000, is about 1:1500, is about 1:1000, is about 1:750, is about 1:500, is about 1:250, is about 1:200, is about 1:150, or is about 1:100. In some embodiments, the concentration of the epoxide is in the range between about 0.1 M and about 5.0 M. In some embodiments, the concentration of the epoxide is in the range between about 0.5 M and about 3.0 M.

In embodiments using a first catalyst to promote the first carbonylation and a second catalyst different from the first catalyst to promote the second carbonylation, the catalysts may be present at a constant ratio and a constant concentration in the reaction vessel or vessels or the concentrations or ratio of the catalysts may be varied during the double carbonylation. The reaction stream may include predominantly only the first catalyst when it enters the reaction vessel, with the second catalyst being introduced at a later point in the process. The first catalyst may be predominantly separated from the intermediate lactone prior to introduction of the second catalyst to the lactone, or, alternatively, the second catalyst may be introduced to the reaction stream without separation of the first catalyst from the lactone. Alternatively, both the first catalyst and the second catalyst may be present in the reaction stream throughout the process.

In some embodiments, the catalyst is preferably present in an amount sufficient to allow the reaction process to be completed in a convenient time interval (e.g. less than about 24 hours, for example less than about 3 hours). In real terms this can require catalyst loadings ranging from about 0.0001 mole percent to about 20 mole percent based on the epoxide substrate. In certain embodiments, the catalyst loading can range from about 0.0001 mole percent to about 1 mole percent, e.g., from about 0.0001 mole percent to about 0.1 mole percent or from about 0.0001 mole percent to about 0.01 mole percent. In certain embodiments, the catalyst loading can range from about 0.001 mole percent to about 20 mole percent, e.g., from about 0.1 mole percent to about 1 mole percent or from about 0.067 mole percent to about 5 mole percent. In some embodiments, the catalyst loading is less than about 0.154 mole percent based on the epoxide substrate. In one such embodiment, the epoxide is ethylene oxide.

In some embodiments, the carbonylation reaction is maintained for a period of time sufficient to allow complete, near complete reaction of the epoxide to acid anhydride or as complete as possible based on the reaction kinetics and or reaction conditions. In some embodiments, the reaction time is maintained for about 24 hours, about 12 hours, about 8 hours, about 6 hours, about 3 hours, about 2 hours or about 1 hour. In some embodiments, the reaction time is established as a residence time within the reactor. The reaction can be halted by reducing the reactor temperature or pressure, withdrawing a particular reactant or introducing a quenching compound. The reaction may be halted at any point or any percentage conversion of epoxide to acid anhydride.

The catalyst or catalysts are preferably recycled from the product stream and returned to the reaction stream after being substantially separated from the acid anhydride product. In some embodiments, the catalyst remains substantially dissolved in the solvent throughout the separation and recycling. In some embodiments, the reaction product is separated by crystallization and filtration. In some embodiments, the catalyst recycling stream is further processed after separation of the product. When two or more catalysts are present, in some embodiments the catalyst recycling stream is further processed to separate the different catalysts into two or more catalyst recycling streams. The separation of the different catalysts may only produce catalyst recycling streams with different ratios of catalyst, or the separation may substantially completely separate the different catalysts. Further processing steps include, but are not limited to, feeding the recycling stream to a flash drum to separate volatiles, drying the recycling stream, heating or cooling the recycling stream, removing spent catalyst, and adding solvent.

Separation

The separation may be accomplished by a variety of separation means, including but not limited to solid-liquid, gas-liquid, and liquid-liquid separation techniques. In some embodiments, the portion of acid anhydride product stream separated is between about 0% and about 100% of the reaction products. The separation can result in a recycle stream comprising solvent and catalyst and an acid anhydride stream. In some embodiments, the separation results in all or nearly all of the reaction catalyst being retained in the recycle stream.

In some embodiments, the temperature reduction of the second reaction product stream 300 is decrease in temperature of between 1% and about 99% from the reaction temperature (on an absolute scale). In some embodiments, the temperature of the second reaction product stream 300 is decreased by between about 1° C. and about 600° C. in the separation step 3. In some embodiments, the pressure or the partial pressure of carbon monoxide of the second reaction product stream 300 is lowered by between about 1 psig and about 5000 psig in the separation step 3.

In some embodiments the separation includes adding a component to the reaction product stream. This component causes a reduction in the solubility of the acid anhydride in the stream, and results in precipitation of the acid anhydride. In some embodiments, the reaction product stream is near or above the saturation point of acid anhydride at particular reaction and reactor exit conditions. In some embodiments, the separation method is crystallization, filtration or sedimentation. Separation may be accomplished with a variety of techniques including but not limited to evaporative cooling crystallization, cooling crystallization, flash drums, drying, filtering and combinations of these techniques.

In some embodiments, the separation includes separating acid anhydride in the vapor phase (e.g., distillation, flashing, etc.,). In some embodiments, separation of the acid anhydride is accomplished through liquid-liquid extraction. The extraction process involves partitioning the reaction product stream into two immiscible solvents. In the extraction, a portion of the acid anhydride will be partitioned into one solvent and the other solvent will contain at least the reaction catalyst. In some embodiments, after the extraction, the solvent containing acid anhydride product will be the acid anhydride product, and the stream containing the catalyst will be recycled.

Carbonylation Reaction Products

In some embodiments, in the carbonylation reaction, un-reacted epoxide may prevent the formation of an acid anhydride. Without being bound by a particular theory, it is speculated that the second carbonylation reaction, converting the beta-lactone to acid anhydride does not proceed, unless all of the epoxide is consumed.

As described above, the reaction product of the double carbonylation reaction is an acid anhydride. In some embodiments, the product is a cyclic anhydride. In some embodiments, the product is succinic anhydride, methylsuccinic anhydride, chloromethylsuccinic anhydride, ethylsuccinic anhydride, or $C_{5-30}$ acid anhydrides. Additionally, the reaction may produce by-products, and the outlet of the reactor may contain un-reacted reactants, as well as catalyst and solvent. In some embodiments, the un-reacted reactants include beta-lactone, epoxide or carbon monoxide. As such, the reaction may not proceed to completion and may be considered a partial reaction.

EXAMPLES

The process parameters of the processes described in FIG. 1 may be modified to optimize the efficiency of the anhydride production. The embodiment of FIG. 1 describes illustrative and non-limiting process parameters suitable for one embodiment of the present invention. In this figure, the solvent used is dioxane and the selected parameters are based on the efficient conversion of epoxide, separation of anhydride, and recycling of catalyst using this solvent. The product stream is about 99.9 wt % succinic anhydride. The gas stream exiting the second PSA unit is about 98.5 wt % CO, about 0.7 wt % methane, and about 0.5 wt % carbon dioxide. The EO, dioxane, and dioxane-catalyst slurry are fed and combined at a pressure of about 225 psia and a temperature of about 30° C. The CO is applied at a pressure of about 210 psia and a temperature of about 100° C. The reaction stream enters the reactor at a pressure of about 215 psia and a temperature of about 50° C., and the product stream exits the reactor at a pressure of about 200 psia and a temperature of about 90° C. The slurry exits the evaporative cooling recrystallizer containing about 25 wt % succinic anhydride at a pressure of about 160 psia and a temperature of about 35° C. The lights vented from the gas stream of the recovery flash drum contain about 3 wt % dioxane, about 21 wt % CO, about 34 wt % methane, and about 42 wt % carbon dioxide.

Carbonylation catalysts and other related experimental details are described in J. Am. Chem. Soc. 2007 (129) pp. 4948-4960 and the supporting information published therewith as well as U.S. Pat. No. 6,852,865 and U.S. Patent Application Publication Nos. 2005/0014977 and 2007/0213524, the entirety of all of which are hereby incorporated herein by reference.

It is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A method of synthesizing an acid anhydride comprising the steps of:
   a) feeding a reaction stream comprising an epoxide, at least one catalyst, at least one solvent, and carbon monoxide to a reaction vessel under reaction conditions to promote a double carbonylation of the epoxide to form dissolved acid anhydride in the reaction vessel, which exits the reaction vessel in a reaction product stream in a continuous flow process;
   b) treating the reaction product stream containing dissolved acid anhydride to conditions that cause the acid anhydride to crystallize such that the reaction product stream comprises crystallized acid anhydride and a liquid phase comprising dissolved catalyst and solvent;
   c) separating the crystallized acid anhydride from the liquid phase; and
   d) recycling the liquid phase comprising dissolved catalyst and solvent to the reaction stream comprising the epoxide;
   wherein the catalyst comprises a transition metal carbonyl compound and further comprises a Lewis acidic co-catalyst.

2. The method of claim 1, wherein step b) occurs in an adiabatic evaporative cooling crystallizer.

3. The method of claim 1, wherein step c) occurs in a rotary drum filter.

4. The method of claim 1, wherein step d) comprises feeding the liquid phase comprising dissolved catalyst and solvent to a recovery flash drum to separate volatiles prior to returning it to the reaction stream.

5. The method of claim 4, further comprising treating the liquid phase by performing at least one step selected from the group consisting of: drying; heating or cooling; removing spent catalyst; adding solvent; and any combination of two or more of these.

6. The method of claim 1, wherein the epoxide is selected from the group consisting of ethylene oxide, propylene oxide, epichlorohydrin, 1,2-butylene oxide, 2,4 butylene oxide, and an oxide of $C_{5-30}$ alpha olefin.

7. The method of claim 6, wherein the epoxide is ethylene oxide.

8. The method of claim 1, wherein the acid anhydride is selected from the group consisting of succinic anhydride, methylsuccinic anhydride, chloromethylsuccinic anhydride, ethylsuccinic anhydride, and $C_{5-30}$ acid anhydrides.

9. The method of claim 8 wherein the acid anhydride is succinic anhydride.

10. The method of claim 1, wherein the first carbonylation reaction is performed at a pressure from about 50 psi to about 5000 psi.

11. The method of claim 1, wherein the first carbonylation reaction is performed at a pressure from about 50 psi to about 2000 psi.

12. The method of claim 1, wherein the first carbonylation reaction is performed at a pressure from about 200 psi to about 1000 psi.

13. The method of claim 1, wherein the first carbonylation reaction is performed at a pressure from about 200 psi to about 600 psi.

14. The method of claim 1, wherein the first carbonylation reaction is performed at a temperature from about 0° C. to about 125° C.

15. The method of claim 1, wherein the first carbonylation reaction is performed at a temperature from about 30° C. to about 100° C.

16. The method of claim 1, wherein the first carbonylation reaction is performed at a temperature from about 40° C. to about 80° C.

17. The method of claim 1, wherein the reaction is operated under steady state reaction conditions.

18. The method of claim 1, wherein the double carbonylation is performed in one or more continuous stirred tank reactors.

19. The method of claim 1, wherein the double carbonylation is performed in one or more plug flow reactors.

20. The method of any one of the preceding claims, wherein the double carbonylation reaction is performed in an adiabatic reactor.

21. The method of claim 20, wherein the adiabatic reactor is a tubular reactor.

22. The method of claim 20, wherein the adiabatic reactor is a shell and tube reactor.

23. The method of claim 1, wherein the solvent is selected from the group consisting of 1,4-dioxane; 1,3-dioxane; tetrahydrofuran; tetrahydropyran; dimethoxyethane; glyme; diethyl ether; t-butyl methyl ether; 2,5-dimethyl tetrahydrofuran; ethyl acetate; propyl acetate; butyl acetate; acetone; 2-butanone; cyclohexanone; toluene; acetonitrile; difluorobenzene and combinations thereof.

24. The method of claim 23, wherein the solvent comprises 1,4-dioxane.

25. The method of claim 1, wherein the at least one catalyst is a single catalyst.

26. The method of claim 25, wherein the single catalyst is $[(ClTPP)Al(THF)_2]^+[Co(CO)_4]^-$, wherein ClTPP is meso-tetra(4-chlorophenyl)porphyrinato and THF is tetrahydrofuran.

27. The method of claim 1, wherein the at least one catalyst comprises a first catalyst selected to promote a first carbonylation of the double carbonylation and a second catalyst different from the first catalyst selected to promote a second carbonylation of the double carbonylation.

28. The method of claim 1, wherein the transition metal carbonyl compound comprises a compound of formula $[M_y(CO)_w]^{x-}$, where:
   M is a transition metal atom
   y is an integer from 1 to 6 inclusive;
   w is a number such as to provide the stable metal carbonyl; and
   x is an integer from −3 to +3 inclusive.

29. The method of claim 28, wherein M is selected from the group consisting of Ti, Cr, Mn, Fe, Ru, Co, Rh, Ni, Pd, Cu and Zn.

30. The method of claim 28, wherein M is Co.

31. The method of claim 28, wherein the transition metal carbonyl compound is anionic, and the Lewis acidic co-catalyst is cationic.

32. The method of claim 31, wherein the transition metal carbonyl compound comprises a carbonyl cobaltate and the Lewis acidic co-catalyst comprises a metal-centered Lewis acid.

33. The method of claim 32, wherein the metal-centered Lewis acid is a metal complex of formula $[M'(L)_b]^{c+}$, where:
   M' is a metal selected from the group consisting of: a transition metal, a group 13 or 14 metal, and a lanthanide;
   each L is a dianionic tetradentate ligand;
   b is an integer from 1 to 6 inclusive;
   c is 1, 2, or 3; and
   where, if more than one L is present, each L may be the same or different.

34. The method of claim 33, wherein M' is selected from the group consisting of: a transition metal, a group 13 or 14 metal, and a lanthanide.

35. The method of claim 33, wherein M' is selected from the group consisting of aluminum, chromium, indium and gallium.

36. The method of claim 33, wherein M' is aluminum.

37. The method of claim 33, wherein M' is chromium.

38. The method of claim 33, wherein the dianionic tetradentate ligand is a ligand comprising a porphyrin; salen; dibenzotetramethyltetraaza[14]annulene (tmtaa); phthalocyaninate; or Trost ligand.

39. The method of claim 1, wherein step c) comprises filtering the reaction product stream.

* * * * *